US00PP35951P2

(12) United States Plant Patent
Bernuetz

(10) Patent No.: US PP35,951 P2
(45) Date of Patent: Jul. 2, 2024

(54) ***SCAEVOLA* PLANT NAMED 'BONSCA 6221'**

(50) Latin Name: *Scaevola aemula*
Varietal Denomination: Bonsca 6221

(71) Applicant: Andrew Bernuetz, Glenbrook (AU)

(72) Inventor: Andrew Bernuetz, Glenbrook (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 18/372,595

(22) Filed: Sep. 25, 2023

(51) Int. Cl.
*A01H 5/02* (2018.01)
*A01H 6/00* (2018.01)

(52) U.S. Cl.
USPC ..... Plt./363
CPC ..... *A01H 6/00* (2018.05)

(58) Field of Classification Search
USPC ..... Plt./363
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Scaevola* plant named 'Bonsca 6221', characterized by its relatively compact and mounding to outwardly spreading plant habit; moderately vigorous growth habit; freely branching habit; early and freely flowering habit; long flowering period; flowers that are dark violet blue in color; and good container and garden performance.

2 Drawing Sheets

Figure 1:
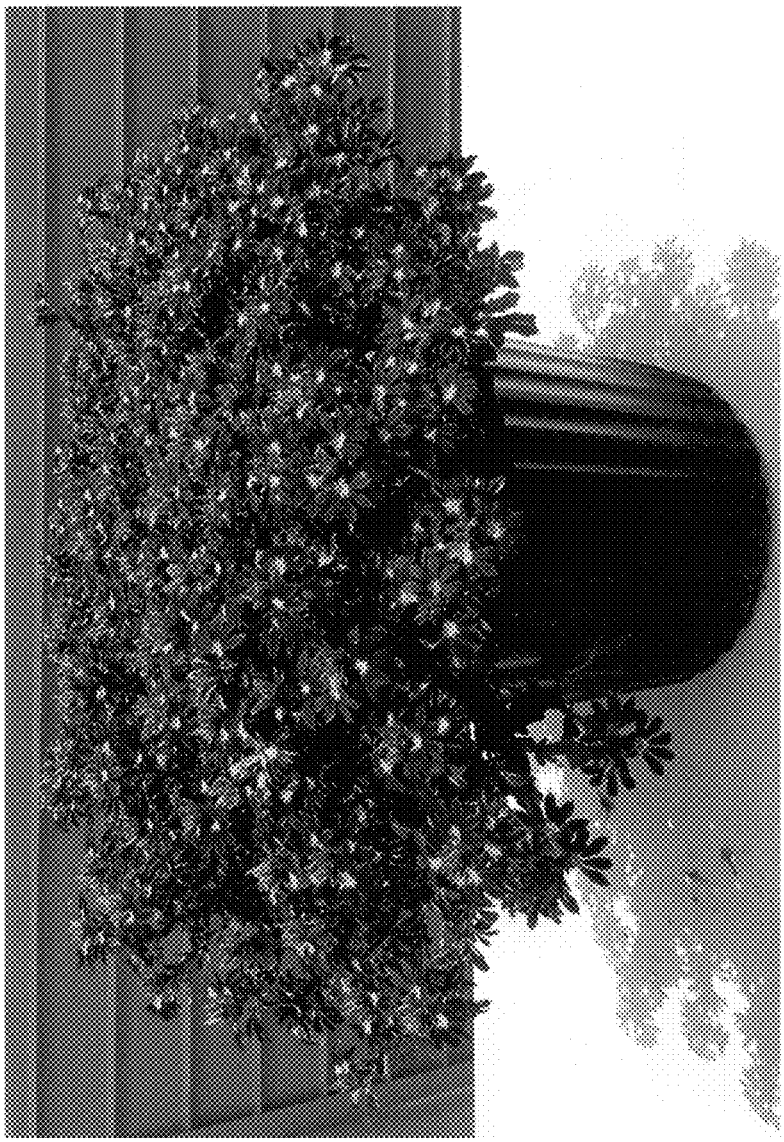

Botanical designation: *Scaevola aemula.*
Cultivar denomination: 'BONSCA 6221'.

BACKGROUND OF THE INVENTION

The present invention relates to a new and distinct cultivar of *Scaevola* plant, botanically known as *Scaevola aemula* and hereinafter referred to by the name 'Bonsca 6221'.

The new *Scaevola* plant a product of a planned breeding program conducted by the Inventor in Yellow Rock, New South Wales, Australia. The objective of the breeding program is to create new compact and mounding *Scaevola* plants with numerous attractive flowers.

The new *Scaevola* plant originated from a cross-pollination conducted by the Inventor in Yellow Rock, New South Wales, Australia in November, 2015 of a proprietary selection of *Scaevola aemula* identified by the code number 14-174, not patented, as the female, or seed, parent with one of two proprietary selections of *Scaevola aemula* (collected as bulk pollen) identified as code numbers 14-178 and 14-206, both not patented, as the male, or pollen, parent. The new *Scaevola* plant was discovered and selected by the Inventor as a single flowering plant from within the progeny of the stated cross-pollination in a controlled greenhouse environment in Yellow Rock, New South Wales, Australia in December, 2016.

Asexual reproduction of the new *Scaevola* plant by vegetative tip cuttings in a controlled greenhouse environment in Yellow Rock, New South Wales, Australia since December, 2016 has shown that the unique features of this new *Scaevola* plant are stable and reproduced true to type in successive generations.

SUMMARY OF THE INVENTION

Plants of the new *Scaevola* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Bonsca 6221'. These characteristics in combination distinguish 'Bonsca 6221' as a new and distinct *Scaevola* plant:

1. Relatively compact and mounding to outwardly spreading plant habit.
2. Moderately vigorous growth habit.
3. Freely branching habit.
4. Early and freely flowering habit.
5. Long flowering period.
6. Flowers that are dark violet blue in color.
7. Good container and garden performance.

Plants of the new *Scaevola* can be compared to plants of the female parent selection. Plants of the new *Scaevola* differ primarily from plants of the female parent selection in flower color as plants of the new *Scaevola* have dark violet blue-colored flowers whereas plants of the female parent selection have blue-colored flowers.

Plants of the new *Scaevola* can be compared to plants of one of the potential male parent selections identified as code number 14-178. Plants of the new *Scaevola* differ primarily from plants of this male parent selection in flower color as plants of the new *Scaevola* have dark violet blue-colored flowers whereas plants of this male parent selection have white-colored flowers. Plants of the new *Scaevola* can be compared to plants of the other potential male parent selection identified as code number 14-206. Plants of the new *Scaevola* differ primarily from plants of this male parent selection in flower color as plants of the new *Scaevola* have dark violet blue-colored flowers whereas plants of this male parent selection have blue-colored flowers.

Plants of the new *Scaevola* can be compared to plants of the *Scaevola aemula* 'Bonsca 1430', disclosed in U.S. Plant Pat. No. 28,820. In side-by-side comparisons, plants of the new *Scaevola* differ from plants of 'Bonsca 1430' in the following characteristics:

1. Plants of the new *Scaevola* are more compact than plants of 'Bonsca 1430'.
2. Plants of the new *Scaevola* are more mounding than and not as spreading as plants of 'Bonsca 1430'.
3. Plants of the new *Scaevola* and 'Bonsca 1430' differ in flower color as flowers of plants of the new *Scaevola* are dark violet blue in color whereas flowers of plants of 'Bonsca 1430' are deep violet in color.

BRIEF DESCRIPTION OF THE PHOTOGRAPHS

The accompanying colored photographs illustrate the overall appearance of the new *Scaevola* plant showing the colors as true as it is reasonably possible to obtain in colored reproductions of this type. Colors in the photographs may differ slightly from the color values cited in the detailed botanical description which accurately describe the colors of the new *Scaevola* plant.

The photograph on the first sheet (FIG. 1) is a side perspective view of a typical flowering plant of 'Bonsca 6221' grown in a container.

Figure 2:
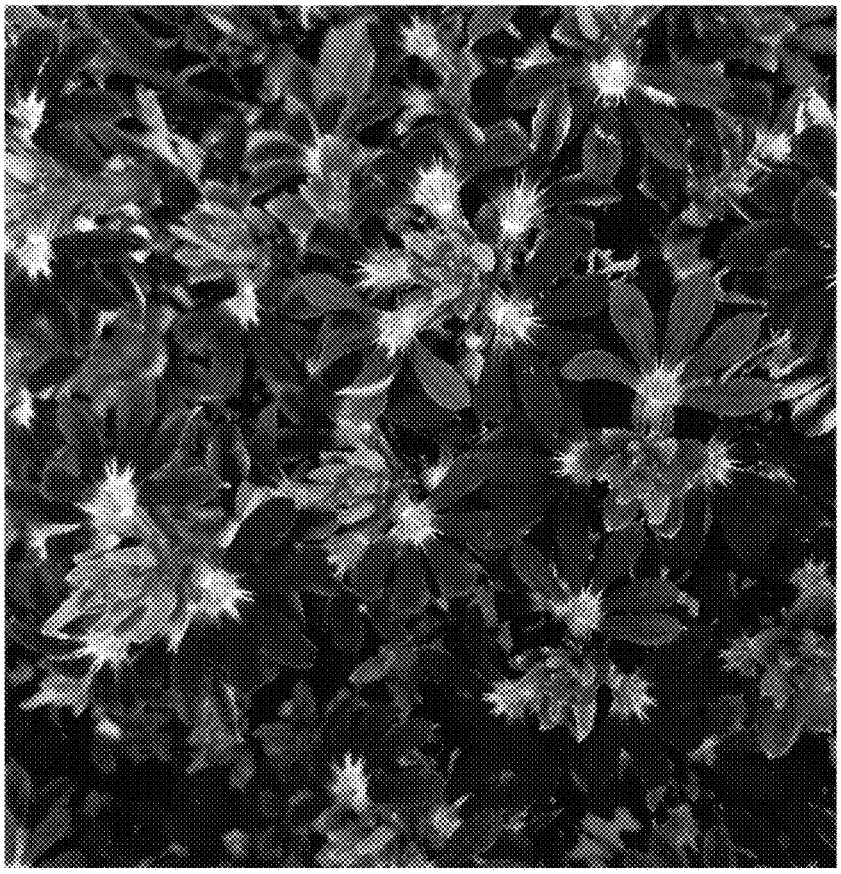

The photograph on the second sheet (FIG. 2) is a close-up view of a typical flowering plant of 'Bonsca 6221'.

DETAILED BOTANICAL DESCRIPTION

The aforementioned photographs and following observations, measurements and values describe plants grown during the summer in 24-cm containers in an outdoor nursery in Higashiomi, Shiga, Japan and under cultural practices typical of commercial *Scaevola* production. During the production of the plants, day temperatures ranged from 15 C to 30 C and night temperatures ranged from 13 C to 25 C. Plants were three months old when the photographs and the detailed description were taken. In the following description, color references are made to The Royal Horticultural Society Colour Chart, 2015 Edition, except where general terms of ordinary dictionary significance are used.

Botanical classification: *Scaevola aemula* 'Bonsca 6221'.

Parentage:

*Female, or seed, parent*.—Proprietary selection of *Scaevola aemula* identified as code number 14-174, not patented.

*Male or pollen parent*.—Proprietary selections of *Scaevola aemula* identified as code number1 14-178 and 14-206, both not patented.

Propagation:

*Type*.—By vegetative tip cuttings.

*Time to initiate roots, summer*.—About ten days at temperatures about 21 C to 25 C.

*Time to initiate roots, winter*.—About 15 days at temperatures about 18 C to 21 C.

*Time to develop roots, summer*.—About three weeks at temperatures about 21 C to 25 C.

*Time to develop roots, winter*.—About four weeks at temperatures about 18 C to 21 C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Relatively compact and mounding to outwardly spreading plant habit; moderately vigorous growth habit.

*Branching habit*.—Freely branching habit with lateral branches potentially forming at every node; pinching enhances branching potential.

*Plant height*.—About 20 cm.

*Plant diameter* (*area of spread*).—About 53 cm.

Lateral branch description:

*Length*.—About 19.2 cm.

*Diameter*.—About 2.2 mm.

*Internode length*.—About 2.2 cm.

*Aspect*.—Upright to outwardly.

*Texture*.—Densely pubescent; rough.

*Color*.—Close to 137C.

Leaf description:

*Arrangement*.—Alternate, simple; sessile.

*Length*.—About 4.4 cm.

*Width*.—About 1.9 cm.

*Shape*.—Spatulate.

*Apex*.—Obtuse.

*Base*.—Attenuate.

*Margin*.—Serrate.

*Texture, upper and lower surfaces*.—Sparsely pubescent; rough.

*Venation pattern*.—Pinnate, reticulate.

*Color*.—Developing leaves, upper surface: Close to NN137A. Developing leaves, lower surface: Close to NN137C. Fully expanded leaves, upper surface: Close to 137B; venation, close to 137C. Fully expanded leaves, lower surface: Close to 137D; venation, close to 139C.

Flower description:

*Flower type and shape*.—Zygomorphic, semi-circular, fan-shaped flowers with five petals fused at the base to form a tubular flower throat; flower throat open along the upper surface exposing the reproductive organs.

*Flower arrangement and quantity*.—Solitary sessile flowers arising from upper leaf axils; flowers mostly horizontal; freely flowering habit with typically about six flowers per lateral branch and about 1,104 flowers developing per plant.

*Flowering time*.—Early flowering habit, plants begin flowering after about three to four weeks after planting; long flower period, plants flower continuously from spring into autumn in Shiga.

*Flower longevity*.—Flowers typically last about a week on the plant; flowers not persistent.

*Fragrance*.—None detected.

*Flower buds*.—Length: About 1.7 cm. Diameter: About 2.6 mm. Shape: Lenticular. Color: Close to 148A.

*Flowers*.—Diameter: About 1.4 cm by 2.5 cm. Depth: About 9.2 mm. Throat diameter: About 3.3 mm. Tube length: About 1.3 cm. Tube diameter, mid-section: About 2.7 mm. Tube diameter, proximally: About 1.9 mm.

*Petals*.—Quantity per flower: Five, fused at base. Length, beyond tube: About 1.3 cm. Width, beyond tube: About 4.6 mm. Shape: Oblanceolate. Apex: Mucronate. Margin: Entire. Texture, upper and lower surfaces: Smooth, glabrous. Texture, throat: Pubescent; rough. Texture, tube: Pubescent; rough. Color: When opening, upper surface: Darker than NN88A.

When opening, lower surface: Close to N87A. Fully opened, upper surface: Close to N89A; venation, close to N89A; color does not change with subsequent development. Fully opened, lower surface: Close to N88B; midrib, close to 196C, and lateral venation, close to N88B; color does not change with subsequent development. Throat: Distally, close to N144D and proximally, close to N144B; venation, close to N77A. Tube: Close to N144D; venation, close to N77C.

*Sepals*.—Quantity per flower: Two, opposite. Length: About 4.2 mm. Width: About 1.7 mm. Shape: Linear. Apex: Acute. Base: Fused. Margin: Entire. Texture, upper and lower surfaces: Pubescent; rough. Color, upper and lower surfaces: Close to 137C.

*Reproductive organs*.—Androecium: Stamen quantity per flower: Five. Filament length: About 5.5 mm. Filament color: Close to 157C. Anther size: About 1.4 mm by 1.7 mm. Anther shape: Ellipsoidal. Anther color: Close to 1D. Pollen: Sparse. Pollen color: Close to 157C. Gynoecium: Pistil quantity per flower: One. Pistil length: About 9 mm. Style color: Close to 145C; hairs, close to N77A. Stigma color: Close to 199C. Ovary color: Close to 144B.

*Seeds and fruits*.—To date, seed and fruit development have not been observed on plants of the new *Scaevola*.

Garden performance: Plants of the new *Scaevola* have been observed to have good garden performance and to tolerate rain, wind and temperatures ranging from about 0 C to about 40 C.

Pathogen & pest resistance: To date, plants of the new *Scaevola* have not been shown to be resistant to pathogens and pests common to *Scaevola* plants.

It is claimed:

1. A new and distinct *Scaevola* plant named 'Bonsca 6221' as illustrated and described.

* * * * *